United States Patent
Prokes et al.

(10) Patent No.: US 7,639,356 B2
(45) Date of Patent: Dec. 29, 2009

(54) HIGHLY EFFICIENT SURFACE ENHANCED RAMAN AND FLUORESCENCE NANOSTRUCTURE SUBSTRATES

(75) Inventors: Sharka M. Prokes, Columbia, MD (US); Orest J. Glembocki, Alexandria, VA (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 12/078,888

(22) Filed: Apr. 8, 2008

(65) Prior Publication Data

US 2008/0285024 A1 Nov. 20, 2008

Related U.S. Application Data

(60) Provisional application No. 60/924,516, filed on May 18, 2007.

(51) Int. Cl.
*G01J 3/44* (2006.01)
(52) U.S. Cl. ...................................... 356/301
(58) Field of Classification Search ................ 356/301; 438/49; 257/E21
See application file for complete search history.

(56) References Cited

U.S. PATENT DOCUMENTS

| | | | |
|---|---|---|---|
| 6,251,249 B1 * | 6/2001 | Chevalier et al. ............. 205/80 |
| 7,158,219 B2 * | 1/2007 | Li et al. ........................ 356/36 |
| 7,245,370 B2 | 7/2007 | Bratkovski | |
| 7,267,948 B2 | 9/2007 | Vo-Dinh | |
| 7,301,624 B2 | 11/2007 | Talley | |
| 7,321,422 B2 | 1/2008 | Li | |
| 7,339,184 B2 * | 3/2008 | Romano et al. ................. 257/1 |
| 2006/0146323 A1 * | 7/2006 | Bratkovski et al. .......... 356/301 |
| 2007/0126116 A1 * | 6/2007 | Dangelo et al. ............. 257/720 |

* cited by examiner

*Primary Examiner*—Gregory J Toatley, Jr.
*Assistant Examiner*—Abdullahi Nur
(74) *Attorney, Agent, or Firm*—Stephen T. Hunnius; John J. Karasek

(57) ABSTRACT

An apparatus comprising a substrate and at least two nanowires on the substrate, the nanowires comprising a core and a metal shell, wherein the core is selected from the group consisting of a semiconductor and a dielectric, thereby forming a nanowire-composite to allow plasmon coupling for enhancements of the electric fields and enhancements of the surface enhanced Raman signal (SERS) and enhancements of the chemical or biological specificity and sensitivity. A method of making a SERS-active substrate comprising providing a substrate and affixing a plurality of nanowires on the substrate thereby forming a nano-composite, creating plasmon coupling leading to enhanced electric fields in the vicinity of the nanowires and enhancements of the surface enhanced Raman signal (SERS) and enhancements of the chemical or biological specificity and sensitivity.

9 Claims, 5 Drawing Sheets

HIGHLY EFFICIENT SURFACE ENHANCED RAMAN AND FLUORESCENCE NANOSTRUCTURE SUBSTRATES

This application claims the benefit of priority to U.S. provisional patent application Ser. No. 60/924,516, filed on May 18, 2007, entitled "Highly efficient surface enhanced raman and fluorescence nanostructure substrates," which is incorporated by reference in its entirety.

Raman scattering is often used in the chemical identification of materials. Light scattered from various vibrational modes in a material is red- and blue-shifted by the frequency of the vibrational modes. The experimental technique then detects the frequency-shifted light. The information that is obtained from Raman scattering is complementary to that of IR spectroscopy, but with the advantage of being performed with visible light. Because the Raman cross-sections of most materials are very small, the intensity of the Raman signal is often 8 orders of magnitude lower than the intensity of the exciting laser. Thus, rapid acquisition of Raman scattering requires the use of intense laser light, limiting the equipment to table top lasers. The situation is even more serious for small amounts of a species adsorbed on a surface of a material.

In the surface enhanced Raman scattering (SERS) effect rough metal surfaces (usually Ag) are used to increase the Raman signal of species adsorbed on the metal. Enhancements of up to 8 orders of magnitude have been observed. The SERS enhancement of molecules adsorbed on the roughened metal surface is caused by local electromagnetic fields that are created by the laser excitation of surface plasmons at the metal surface. Significant work has been done in SERS using various metals and geometry for the roughened features, including aggregate films, nano-particles, nano-shells and solid metal nanowire ordered arrays.

It has been shown that local hot spots in the electric fields produced by localized plasmons excited in nanoparticles can produce large SERS effects[1]. Furthermore, it has been suggested that using nanoparticles of appropriate size and geometry can lead to further enhancements by moving the plasmons absorption frequency close to that of the exciting laser. This adds resonant enhancement to the SERS process, further increasing the Raman signal.

DESCRIPTION

The disclosure describes a new SERS-active substrate consisting of dielectric/Ag nanowire composites, which show very enhanced sensitivities, in the parts per billion range. The reason for such high sensitivities can be that the nanowire crossings lead to very large electric field enhancements in large regions around the nanowires, allowing a larger volume of molecules of interest to be detected.

Furthermore, the wires can also be dispersed in a liquid, allowing for stand-off sensing applications.

Still furthermore, the nanowires can serve as taggants.

The disclosure describes metal/wide band gap semiconductor nanowire composites, and method of making, which exhibit significantly enhanced surface enhanced Raman scattering (SERS) and fluorescence (SEF) signal and which can be used for very efficient chemical or biological sensors.

In one embodiment, the fabrication technique can be applicable to $Ga_2O_3$ semiconductor nanowires and other metal oxide nanowires, with controlled size diameters ranging from about 5 to about 100 nm. The composite can consist of the nanowire core structure, which can be coated with a silver metallic shell on the order of 3-10 nm.

Raman scattering molecular fluorescence can be enhanced by the adsorption of molecules on metal nanostructures. As in SERS, SEF also relies on the electric fields to increase the signal strengths. Use of a laser frequency within the surface plasmon absorption band would produce enhanced fluorescence. The intersections of wires produce coupled plasmon resonances whose strength and width is significantly greater than that of the individual wires. This in turn leads to enhanced fluorescence.

Figure 1:
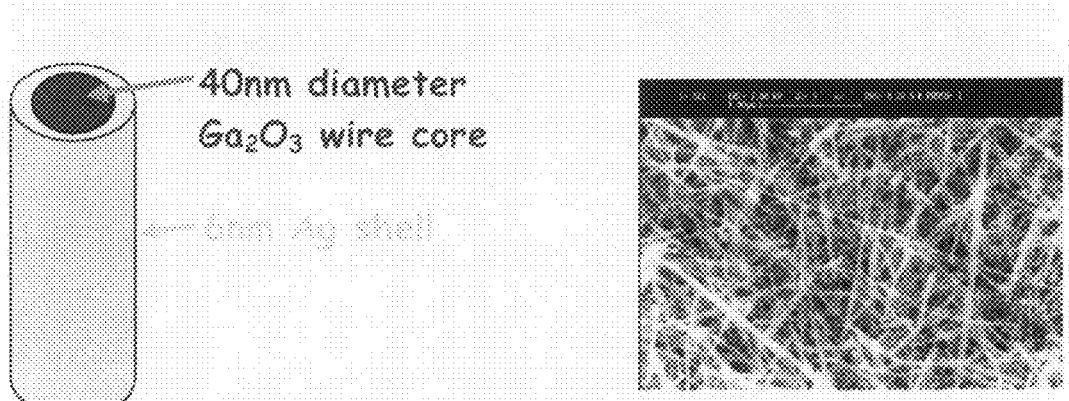
FIG. 1 $Ga_2O_3$ core/Ag shell nanowire composite drawing and SEM image.

This disclosure describes a SERS/SEFS substrate which consists of a wide band gap semiconductor nanowire/metal shell nano-composite (FIG. 1) which allows shifting of the plasmon absorption nearer to exciting laser line, combined with the formation of a high density of "hot" spots by creating a random (FIG. 2) or ordered 3D wire array, where a high density of wire crossings can be achieved.

In another example, the wires can be fabricated in a tube furnace which has a base vacuum of 20 mTorr. The wire growth can proceed by the vapor-liquid-solid (VLS) growth mechanism, using a solid Ga source, a flow of oxygen gas, and 10-20 nm of gold on any substrate can be used as the catalyst. A size controlled Au colloid can also be used to obtain wires of uniform diameters, ranging from about 5 nm to about 100 nm.

The wires can be removed from the substrate by sonication in an ethanol solution and deposited on a clean and dry substrate appropriate for SERS/SEFS. The metal shell coating can be deposited via e-beam evaporation or electroless solution deposition. In this embodiment, any metal can be used. The SERS/SEFS sensitivity of the formed substrate has been determined using a Rhodamine 6G solution of various molarities. It has been observed that these nanowires can produce a SERS signal in dilutions as low as $10^{-9}$M of Rhodamine dissolved in methanol.

Figure 2:
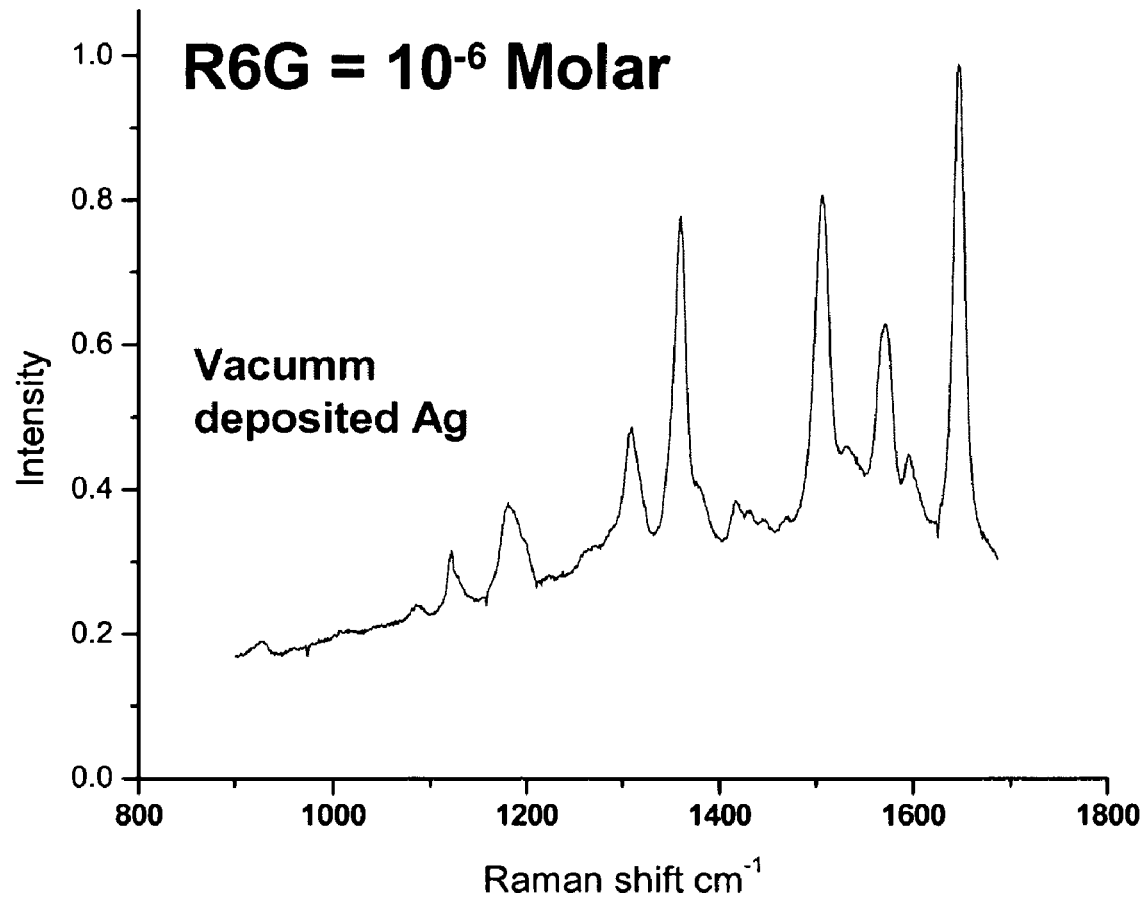
FIG. 2 SERS signal from nanowire/Ag composite SERS substrate. Molecule used for detection is Rhodamine 6G.
Figure 3:
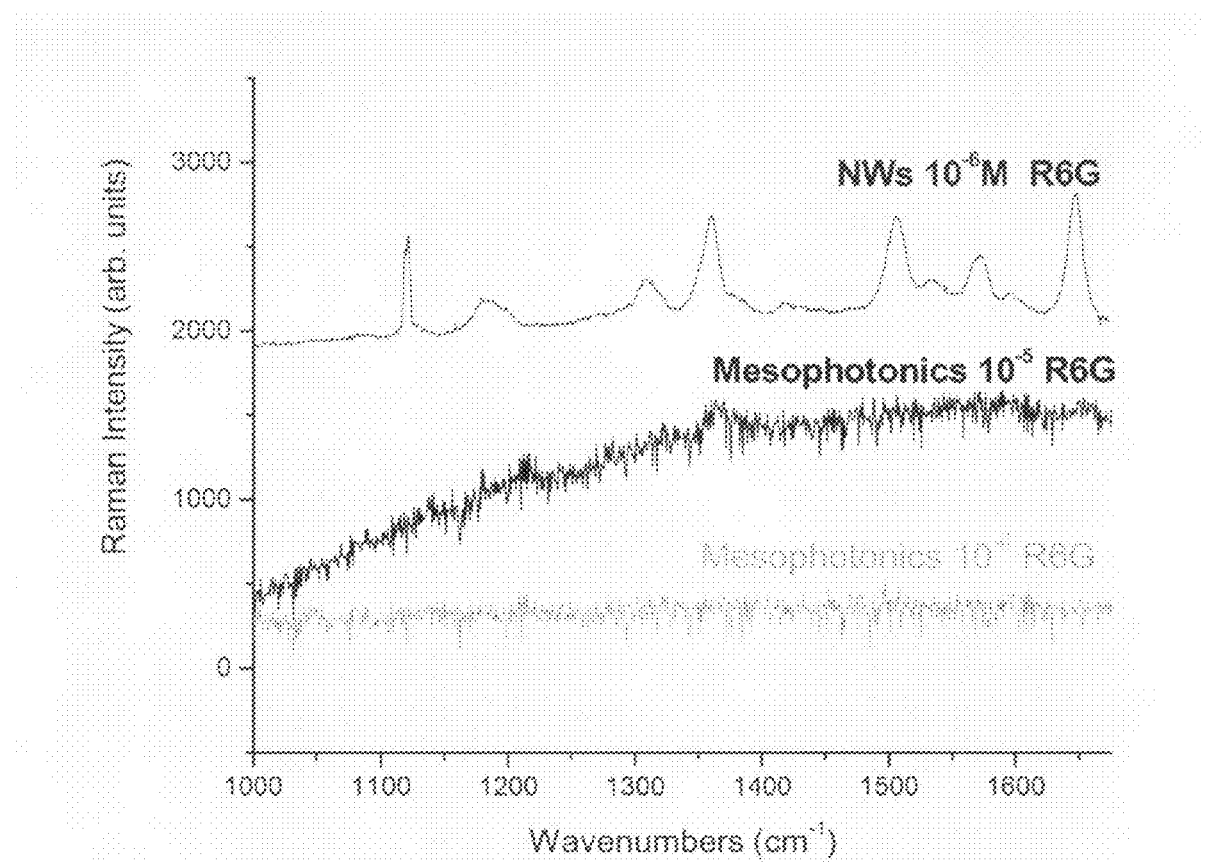
FIG. 3 Comparison of SERS signal for Mesophotonics "Klarite" commercial substrate and our $Ga_2O_3$/Ag nanowire composites.

While Rhodamine 6G was used, any other chemical species can also work. A SERS signal from the nanowire/Ag composite substrate is shown in FIG. 2. A commercially available SERS substrate from Mesophotonics (Klarite) has been measured for SERS enhancement using R6G, and a comparison of the sensitivity is shown in FIG. 3. As can be seen, no SERS signal can be seen for $10^{-6}$M Rhodamine in the case of the commercial Mesophotonics sample, while a strong SERS signal is shown for the nanowire composites, measured under the same conditions.

If $10^{-5}$ M rhodamine is used, the Mesophotonics sample exhibits a very weak SERS signal, shown in FIG. 3. Thus, from these results, the nanowire/Ag composite substrate can repeatably exhibit an enhancement which is roughly a factor of 35 higher than the commercially available SERS substrate.

The SERS and SEF signal has been measured to be several orders of magnitude more sensitive using the nanowire/metal random 3D arrays than currently available SERS or SEFS substrates, including Ag nanosphere arrays produced by the Tollen's reaction, SiO$_2$/Ag nanosphere composites, polystyrene/Ag nanosphere composites, as well as roughened metal surfaces and commercially available SERS substrates from Mesophotonics ("Klarite"). In addition, these wires have exhibited sensitivity to DNT better than picograms, which can be quite difficult for any SERS substrate, due to the very low vapor pressure of DNT.

In another embodiment, the nanowires can be grown by a vapor process, a vapor-liquid-solid mechanism, or an oxide-based mechanism.

Another aspect can be that the crossed wires that can be produced by this technique can increase the enhancement in the vicinity of the regions where wires cross. The angle of the crossed wires can determine the strength and position of the improved enhancement. The crossing of the nanowires can lead to coupled plasmonic behavior that spatially extends the sensitivity of the nanowires to encompass the regions between the wires and significantly beyond the wires.

The sensitivity regions can be within a sphere whose diameter can be the length of the longest wire, which is a significant improvement over nanosphere-type SERS substrates.

The density of wires can be such that 2 nanowires are in a micron by micron area.

Another embodiment can be such that the wires are parallel to each other and separated by 100 nm or less.

Figure 4:
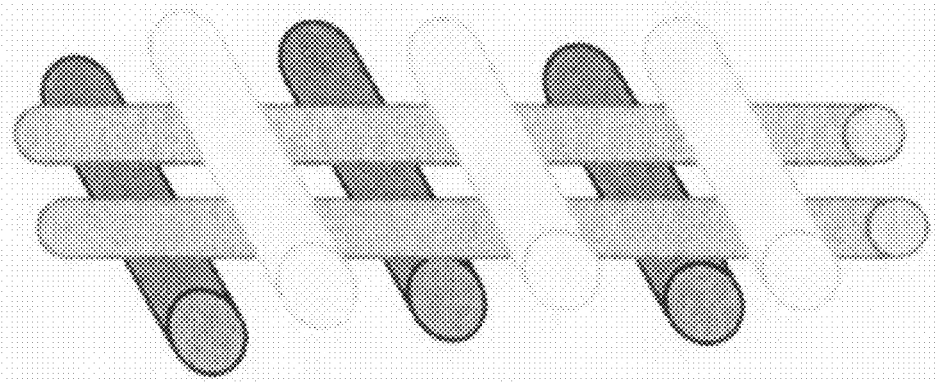
FIG. 4 Schematic diagram showing how crossed nanowires can be used to construct a 3D array that may maximize crossing points, where the SERS enhancement may be greatest.

By a judicious distribution of these nanowires, it can be possible to produce a SERS/SEFS substrate that can be an open 3D network that can have many layers of crossed wires, as shown in FIG. 4. This configuration would allow for a SERS/SEFS substrate that would sense a gas or liquid in 3D and allow light to sense through the substrate. This can be possible, since the strongest enhancements occur between wire crossing and light can pass through this region without being lost to scattering by the adjacent wire or absorption by the nanowires. The use of metal nanoshells as in this disclosure reduces the absorption losses that plague solid metal nanospheres or nanowires, enabling the 3D sensing described above.

Figure 5:
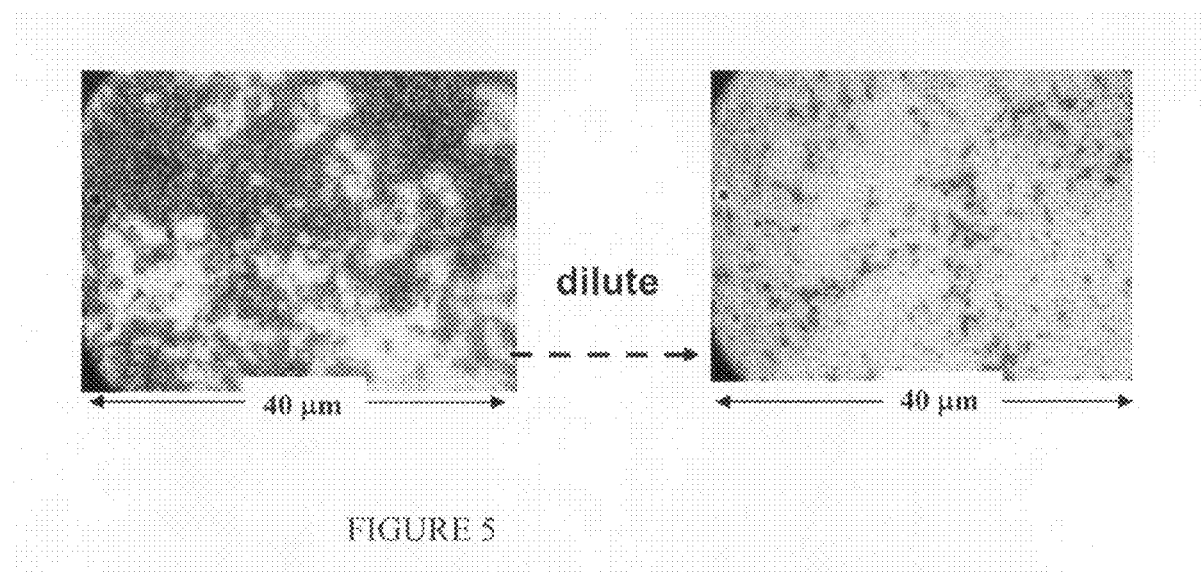
FIG. 5 Dilution of $Ga_2O_3$/Ag nanowire composites.

Due to these highly efficient "hot" spot regions formed by the crossing of the nanowires, it has been demonstrated that large SERS enhancements can be possible even when the density of the nanowire network is significantly reduced. An optical image of the wire density reduction is shown in FIG. 5 below.

The SERS signal measured for the dilute sample shown in FIG. 4 resulted in a factor of 3 drop of the SERS intensity. Since the enhancements are on the order of 10$^7$, the factor of 3 decrease can be considered minor. Since these wires can be deposited at low concentrations on any substrate and any size area, they can provide for potential applications in large area sensor arrays and remote sensing applications, where the SERS material could be delivered in liquid form onto any surface. Furthermore, due to the low density requirement, the fabrication and delivery of these SERS nanowire composite materials can be extremely cheap and efficient.

Possible alternatives include other substrates such as Ag nanoparticles and commercially available Mesophotonics "Klarite" SERS substrates.

The above description is that of a preferred embodiment of the invention. Various modifications and variations are possible in light of the above teachings. It is therefore to be understood that, within the scope of the appended claims, the invention may be practiced otherwise than as specifically described. Any reference to claim elements in the singular, e.g., using the articles "a," "an," "the," or "said" is not construed as limiting the element to the singular.

What we claim is:

1. An apparatus comprising:
   a mechanically stable substrate selected from the group consisting of a semiconductor, metal, and dielectric; and
   at least two nanowires on the substrate, the nanowires comprising a core and a metal shell, wherein the core is selected from the group consisting of a semiconductor and a dielectric, thereby forming a nanowire-composite to allow plasmon coupling for enhancements of the electric fields and enhancements of the surface enhanced Raman signal (SERS) and enhancements of the chemical or biological specificity and sensitivity;
   wherein the at least two nanowires comprises a plurality of nanowires;
   wherein the plurality of nanowires is a random or ordered three dimensional wire array forming a high density of nanowires for enhanced sensitivities;
   wherein the nanowires are selected from the group consisting of Ga$_2$O$_3$, ZnO, SiO$_2$, InAs, InSb, SiC and GaN;
   wherein the metal shell is Ag or Au and is formed by e-beam evaporation or electroless solution-based deposition;
   wherein the nanowires have a diameter of from about 30 nm to about 150 nm and are grown by one selected from the group consisting of a vapor process, a vapor-liquid-solid mechanism, and an oxide-assisted mechanism:
   wherein the density of the at least two nanowires is 2 nanowires in a micron by micron area.

2. The apparatus of claim 1 wherein the nanowires have a diameter of about 40 nm.

3. The apparatus of claim 1 wherein the metal shell has a thickness of about 6 nm.

4. The apparatus of claim 1 wherein the metal shell has a thickness of from about 3 nm to about 20 nm.

5. The apparatus of claim 4 wherein a SERS signal is produced in dilutions as low as 10$^{-9}$ M of Rhodamine dissolved in methanol and where ppb or less of benzene thiol and DNT can be detected.

6. The apparatus of claim 1 wherein the at least two nanowires are parallel to each other and separated by 100 nm or less.

7. A method of making a SERS-active substrate comprising:
   providing a mechanically stable substrate selected from the group consisting of a semiconductor, metal, and dielectric;
   affixing a plurality of nanowires on the substrate wherein the nanowires are comprised of one selected from the group consisting of Ga$_2$O$_3$, ZnO, SiO$_2$, InAs, InSb, SiC and GaN having a diameter of between about 30 nm to about 150 nm, and a metal shell thereby forming a nanocomposite;
   wherein the nanowires are grown by one selected from the group consisting of a vapor process, a vapor-liquid-solid mechanism, and an oxide-assisted mechanism;
   wherein the metal shell is Ag or Au and if formed by e-beam evaporation or electroless solution-based deposition;
   wherein the plurality of nanowires is a random or ordered three dimensional wire array forming a high density of nanowires for enhanced sensitivities;
   wherein the density of the plurality of nanowires is 2 nanowires in a micron by micron area; and
   creating plasmon coupling leading to enhanced electric fields in the vicinity of the nanowires and enhancements of the surface enhanced Raman signal (SERS) and enhancements of the chemical or biological specificity and sensitivity.

8. The method according to claim 6 further comprising: exposing the nanowires to laser light and inducing plasmon coupling and enhanced electric fields to sense a gas or liquid.

9. The method according to claim 7 wherein the metal shell is Ag or Au having a diameter of from about 3 nm to about 20 nm wherein the metal shell is formed by e-beam evaporation or electroless solution-based deposition.

* * * * *